United States Patent
Petroff

(10) Patent No.: US 10,028,725 B2
(45) Date of Patent: Jul. 24, 2018

(54) FRICTION TORQUE LIMITER FOR AN IMAGING CATHETER

(71) Applicant: LIGHTLAB IMAGING, INC., Westford, MA (US)

(72) Inventor: Christopher Petroff, Groton, MA (US)

(73) Assignee: LIGHTLAB IMAGING, INC., Westford, MA (US)

( * ) Notice: Subject to any disclaimer, the term of this patent is extended or adjusted under 35 U.S.C. 154(b) by 253 days.

(21) Appl. No.: 14/768,804

(22) PCT Filed: Mar. 11, 2013

(86) PCT No.: PCT/US2013/030166
§ 371 (c)(1),
(2) Date: Aug. 19, 2015

(87) PCT Pub. No.: WO2014/163601
PCT Pub. Date: Oct. 9, 2014

(65) Prior Publication Data
US 2016/0000406 A1   Jan. 7, 2016

(51) Int. Cl.
*A61B 8/00* (2006.01)
*A61B 8/12* (2006.01)
(Continued)

(52) U.S. Cl.
CPC ......... *A61B 8/445* (2013.01); *A61B 5/0066* (2013.01); *A61B 5/0084* (2013.01); *A61B 8/12* (2013.01);
(Continued)

(58) Field of Classification Search
CPC ......... A61B 8/445; A61B 8/12; A61B 8/4461; A61B 5/0066; A61B 5/0084; F16D 7/021;
(Continued)

(56) References Cited

U.S. PATENT DOCUMENTS 2,050,630 A   8/1936   Reid
2,773,369 A   12/1956  Klemm
(Continued)

FOREIGN PATENT DOCUMENTS

EP   0387980 A1   9/1990
EP   0445918      9/1991
(Continued)

OTHER PUBLICATIONS

International Search Report and Written Opinion for International Patent Application No. PCT/US2010/061613, dated Feb. 22, 2011, 9 pages.
(Continued)

*Primary Examiner* — Bo J Peng
(74) *Attorney, Agent, or Firm* — K&L Gates LLP

(57) ABSTRACT

The invention provides a frictional torque limiter assembly for an imaging core spinning in a patient's body. The torque limiter assembly torsionally isolates the imaging core from a motor that spins the imaging core. An interference fit between a slitted drive tube and a spacer tube acts as a clutch that allows a spinning imaging probe to slow or stop relative to the motor until the motor is stopped, thereby preventing an unsafe condition.

20 Claims, 21 Drawing Sheets

(51) Int. Cl.
*A61B 5/00* (2006.01)
*F16D 7/02* (2006.01)
*F16D 43/21* (2006.01)
*A61M 25/01* (2006.01)

(52) U.S. Cl.
CPC ....... *A61B 8/4461* (2013.01); *A61M 25/0138* (2013.01); *A61M 25/0147* (2013.01); *F16D 7/021* (2013.01); *F16D 43/211* (2013.01)

(58) Field of Classification Search
CPC ............. F16D 43/211; A61M 25/0138; A61M 25/0147
See application file for complete search history.

(56) References Cited

U.S. PATENT DOCUMENTS

| | | |
|---|---|---|
| 3,306,291 A | 2/1967 | Burke |
| 4,266,815 A | 5/1981 | Cross |
| 4,434,904 A | 3/1984 | D'Amico et al. |
| 4,669,999 A | 6/1987 | Miller |
| 4,971,267 A | 11/1990 | Fulton et al. |
| 5,185,004 A * | 2/1993 | Lashinski ......... A61M 25/0136 600/434 |
| 5,228,441 A | 7/1993 | Lundquist |
| 5,321,501 A | 6/1994 | Swanson et al. |
| 5,368,480 A | 11/1994 | Balfour et al. |
| 5,459,570 A | 10/1995 | Swanson et al. |
| 5,465,147 A | 11/1995 | Swanson |
| 5,509,093 A | 4/1996 | Miller et al. |
| 5,596,996 A | 1/1997 | Johanson et al. |
| 5,619,368 A | 4/1997 | Swanson |
| 5,748,598 A | 5/1998 | Swanson et al. |
| 5,784,352 A | 7/1998 | Swanson et al. |
| 5,820,614 A | 10/1998 | Erskine et al. |
| 5,913,437 A | 6/1999 | Ma |
| 5,956,355 A | 9/1999 | Swanson et al. |
| 6,111,645 A | 8/2000 | Tearney et al. |
| 6,134,003 A | 10/2000 | Tearney et al. |
| 6,160,826 A | 12/2000 | Swanson et al. |
| 6,191,862 B1 | 2/2001 | Swanson et al. |
| 6,282,011 B1 | 8/2001 | Tearney et al. |
| 6,421,164 B2 | 7/2002 | Tearney et al. |
| 6,445,939 B1 | 9/2002 | Swanson et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 * | 5/2003 | Pitris ................. A61B 1/00172 600/478 |
| 6,570,659 B2 | 5/2003 | Schmitt |
| 6,582,368 B2 | 6/2003 | Holdaway et al. |
| 6,706,004 B2 | 3/2004 | Tearney et al. |
| 6,879,851 B2 | 4/2005 | McNamara et al. |
| 6,891,984 B2 | 5/2005 | Petersen et al. |
| 7,066,819 B2 | 6/2006 | Ueda et al. |
| 7,121,947 B2 | 10/2006 | Ueda et al. |
| 7,208,333 B2 | 4/2007 | Flanders et al. |
| 7,231,243 B2 | 6/2007 | Tearney et al. |
| 7,241,286 B2 | 7/2007 | Atlas |
| 7,311,625 B2 | 12/2007 | Nosaka et al. |
| 7,407,440 B2 | 8/2008 | White |
| 7,414,779 B2 | 8/2008 | Huber et al. |
| 7,415,049 B2 | 8/2008 | Flanders et al. |
| 7,625,366 B2 | 12/2009 | Atlas |
| 7,813,609 B2 | 10/2010 | Petersen et al. |
| 7,848,791 B2 | 12/2010 | Schmitt et al. |
| 7,916,387 B2 | 3/2011 | Schmitt |
| 7,935,060 B2 | 5/2011 | Schmitt et al. |
| 2002/0151799 A1 | 10/2002 | Pantages et al. |
| 2002/0161351 A1 | 10/2002 | Samson et al. |
| 2004/0186368 A1 | 9/2004 | Ramzipoor et al. |
| 2005/0201662 A1 | 9/2005 | Petersen et al. |
| 2006/0095065 A1 | 5/2006 | Tanimura et al. |
| 2007/0232892 A1 | 10/2007 | Hirota |
| 2007/0232893 A1 | 10/2007 | Tanioka |
| 2007/0250036 A1 * | 10/2007 | Volk ................. A61M 25/0009 604/510 |
| 2007/0260227 A1 | 11/2007 | Phan |
| 2008/0097293 A1 * | 4/2008 | Chin ................... A61B 1/0055 604/95.04 |
| 2009/0174931 A1 | 7/2009 | Huber et al. |
| 2009/0292199 A1 * | 11/2009 | Bielewicz ............... A61B 8/12 600/424 |
| 2009/0306520 A1 | 12/2009 | Schmitt et al. |
| 2010/0076320 A1 | 3/2010 | Petersen et al. |
| 2010/0094127 A1 | 4/2010 | Xu |
| 2010/0253949 A1 | 10/2010 | Adler et al. |
| 2011/0007315 A1 | 1/2011 | Petersen et al. |
| 2011/0071404 A1 | 3/2011 | Schmitt et al. |
| 2011/0071405 A1 | 3/2011 | Judell et al. |
| 2011/0101207 A1 | 5/2011 | Schmitt |
| 2011/0151980 A1 | 6/2011 | Petroff |
| 2011/0251519 A1 * | 10/2011 | Romoscanu ...... A61M 25/0013 600/585 |
| 2014/0142553 A1 | 5/2014 | Poncon |

FOREIGN PATENT DOCUMENTS

| | | |
|---|---|---|
| JP | 07-184888 | 7/1995 |
| JP | 10-66696 | 3/1998 |
| WO | 2007139457 | 12/2007 |
| WO | 2008121234 | 10/2008 |

OTHER PUBLICATIONS

Mondofacto, Charrie Scale, [online] Mar. 5, 2000 [retrieved Feb. 1, 2012]. Retrieved from the Internet URL: http://www.mondofacto.com/facts/dictionary?Charriere+scale.

PCT Written Opinion for PCT International Patent Application No. PCT/US2013/030166, dated Jun. 12, 2014 (5 pages).

PCT International Search Report for PCT International Patent Application No. PCT/US2013/030166, dated Jun. 12, 2014 (3 pages).

* cited by examiner

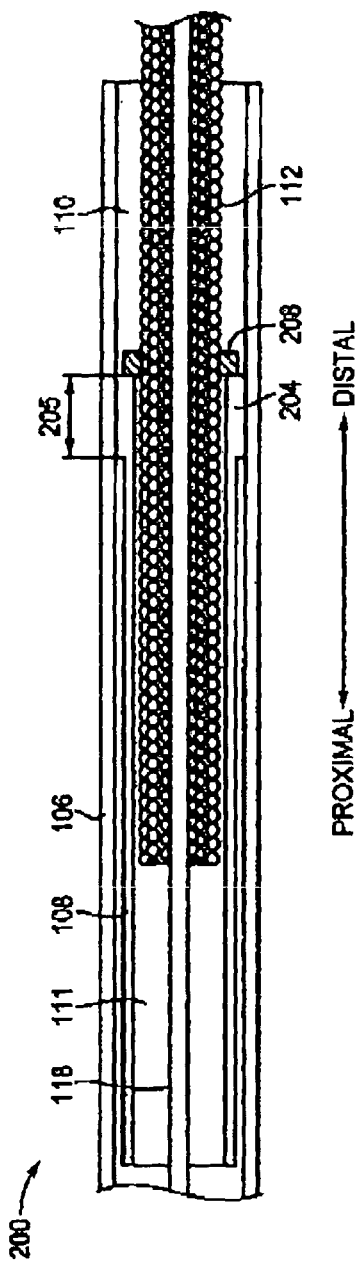
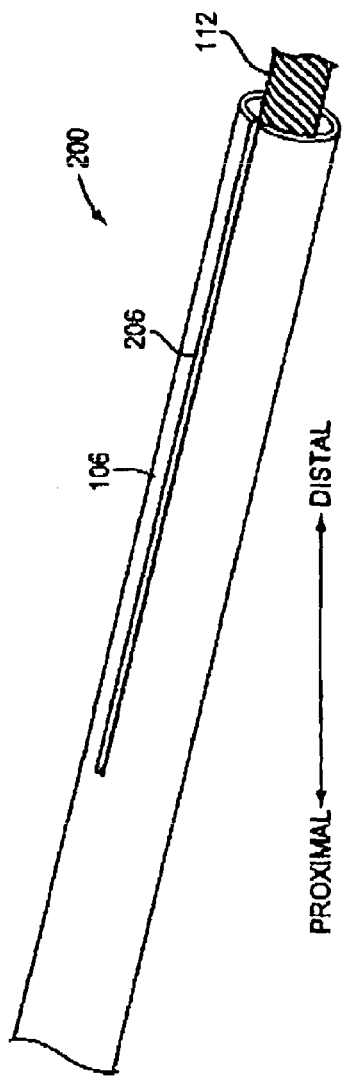
FIG. 2A
FIG. 2B

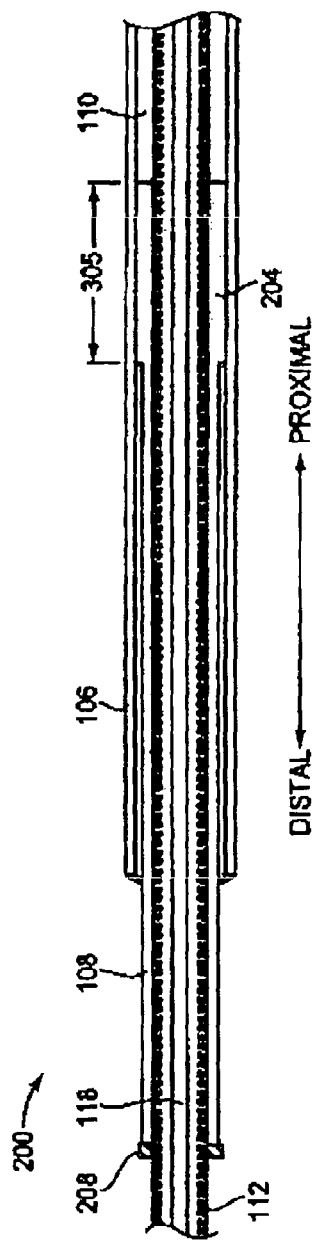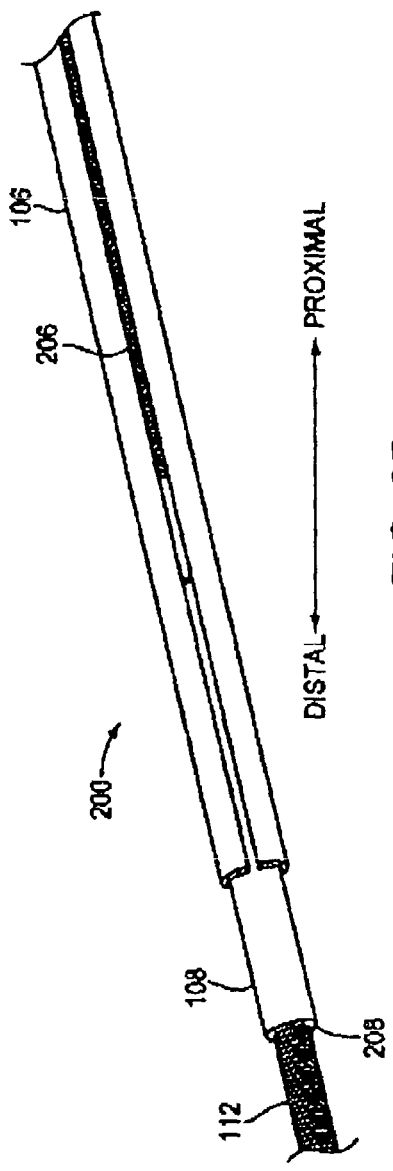
FIG. 3A
FIG. 3B

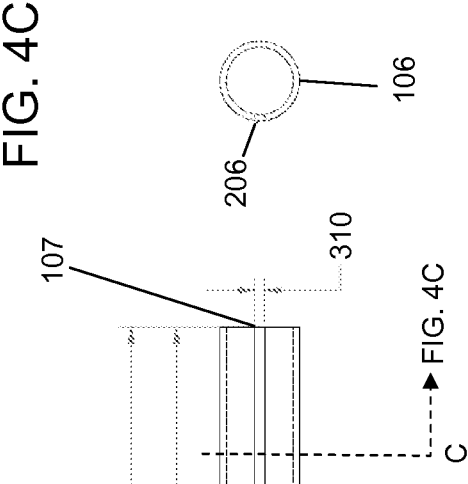
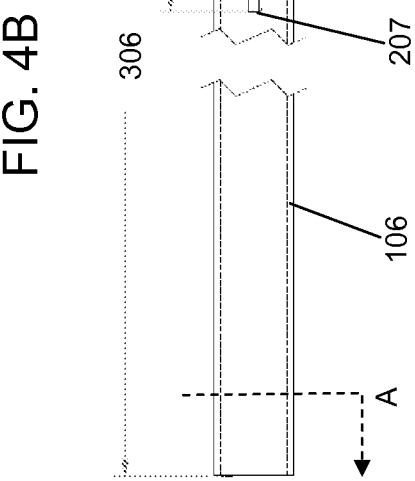
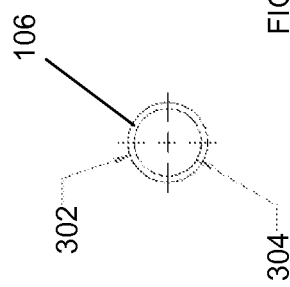

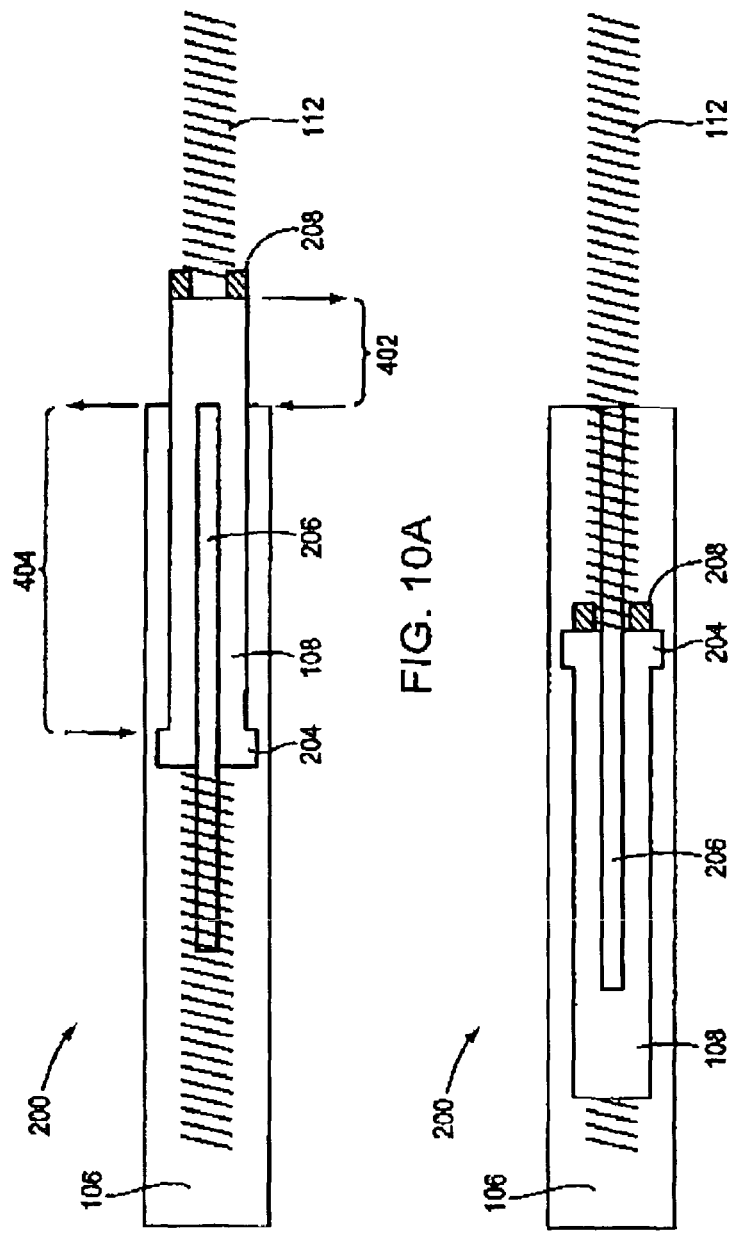

FRICTION TORQUE LIMITER FOR AN IMAGING CATHETER

CROSS REFERENCE TO RELATED APPLICATIONS

This is the national phase under 35 U.S.C. § 371 of International Application No. PCT/US2013/030166 filed on Mar. 11, 2013, the entire disclosure of which is incorporated by reference herein.

TECHNICAL FIELD

Provided are devices and methods for limiting the rotational force imparted on an imaging probe spinning inside a patient to reduce the likelihood of an unsafe condition should the imaging probe suddenly bind but still provides sufficient rotational force when there are no unsafe conditions.

BACKGROUND

Imaging of body lumens (e.g., vasculature) can require relatively high torque and relatively high rotational speeds to spin an imaging probe, such as an optical coherence tomography (OCT) probe, intravascular ultrasound probe (IVUS), or fractional flow reserve probe (FFR), inside the body lumen. Generally, an imaging probe is inserted in a body lumen of a patient and a motor located outside the patient spins a torque wire which is connected to the imaging probe. Imaging systems have unique torque wire requirements as the optical fiber rotates with the torque wire, adding mass and stiffness. However, high torque and high speed rotation can pose a significant risk of patient harm should the imaging probe unexpectedly bind because the motor will continue spinning the torque wire and the binding will spin the catheter sheath which encloses the torque wire inside the body lumen, potentially causing patient harm.

SUMMARY

The invention relates, in part, to a frictional torque limiter assembly for an imaging core spinning in a patient's body. The torque limiter assembly torsionally isolates the imaging core from a motor that spins the imaging core. The motor is connected to an optical connector which, in turn, is directly or indirectly connected to a drive tube. A spacer tube is secured in the lumen of the drive tube by interference fit. The interference fit is made possible by an axial slit in the drive tube that extends from one end partially along the length of the drive tube. The spacer tube is connected to a torque wire which, in turn, is attached to the imaging probe. An optic fiber or wire is disposed in the torque wire and connects the optical connector to the imaging probe. During imaging, the optical connector, the drive tube, the spacer tube, the torque wire, and the imaging probe spin in unison. The interference fit between the spacer tube and the drive tube is configured such that, if the torque wire or the imaging probe binds, the spacer tube slips within the drive tube. The spacer tube therefore acts as a clutch that allows torque wire to stop or spin at a slower rate than drive tube until the motor is stopped, thereby preventing an unsafe condition.

The invention provides, in part, a torque limiter for an intravascular imaging probe. The torque limiter includes a drive tube. The drive tube has a wall that defines a drive tube lumen having an inside diameter. The drive tube wall defines or forms a slit extending from a first end of the drive tube lumen along a portion of the drive tube wall. The torque limiter also includes a spacer tube received in the first end of the drive tube lumen. The spacer tube has a spacer tube wall that defines an outside diameter. At least a portion of the spacer tube wall is in interference fit with the inside diameter of the drive tube wall. In addition, the torque limiter includes a torque wire attached to the spacer tube. Accordingly, the spacer tube spins within the drive tube if torque on the torque wire exceeds a predetermined threshold, thereby preventing an unsafe patient condition.

In some embodiments, the spacer tube wall forms a circumferential collar and the circumferential collar is interference fit with the inside diameter of the drive tube wall. The circumferential collar can be located at an end of the spacer tube, or the circumferential collar can be located between the ends of the spacer tube, such as at or near the center of the spacer tube. The circumferential collar also can have a chamfered edge to facilitate insertion into the drive tube during assembly.

In some embodiments, substantially the entire spacer tube wall is interference fit with the inside diameter of the drive tube wall. In some embodiments, the slit extends axially along the drive tube wall. In some embodiments, the device includes an optical coherence tomography probe coupled to an optical fiber disposed in the torque wire. In some embodiments, the device includes an intravascular ultrasound probe. In some embodiments, the interference fit has a torsional strength of about 0.1 ounce-inches to about 0.4 ounce-inches. In some embodiments, the slit is wider at its closed end than at its open end. In some embodiments, the drive tube wall has a thickness and the thickness is reduced along at least a portion of the slit. In some embodiments, the drive tube wall forms a slot parallel to the slit, the slot having closed ends.

The invention relates, in part, to a torque limiter for an intravascular imaging probe. The torque limiter includes a clutch that includes a first rotatable tube defining a first bore, the first tube comprising a first tube wall defining a slit extending from a first end of the first rotatable tube, the first rotatable tube having a length T1; and a second rotatable tube defining a second bore, the second tube comprising a second tube wall, the first rotatable tube having a length T2, the second rotatable tube disposed within the first rotatable tube such that the first bore is substantially concentric with the second bore, the second bore aligned to receive a torque wire below the slit, the second rotatable tube clutched by the first tube wall on either side of the slit such that the second rotatable tube is configured to slip or rotate if a torque on the torque wire exceeds a predetermined threshold. The torque limiter can further include the torque wire.

In one embodiment, T1 is greater than T2. In one embodiment, the slit is wider at its closed end than at its open end. In one embodiment, the second rotatable tube is interference fit within the first rotatable tube. In one embodiment, the interference fit has a torsional strength of about 0.1 ounce-inches to about 0.4 ounce-inches. In one embodiment, the second tube wall includes a circumferential collar interference fit with an inside diameter of the first bore.

BRIEF DESCRIPTION OF DRAWINGS

The figures are not necessarily to scale, emphasis instead generally being placed upon illustrative principles. The figures are to be considered illustrative in all aspects and are not intended to limit the invention, the scope of which is defined only by the claims.

FIG. 2A shows a longitudinal cross-section of a torque limiter assembly.

FIG. 2B shows a perspective view of a torque limiter assembly.

FIG. 3A shows a longitudinal cross-section of a torque limiter assembly having an inverted spacer tube.

FIG. 3B shows a perspective view of a torque limiter assembly having an inverted spacer tube.

FIG. 4A is a schematic showing a transverse cross-section of the drive tube along plane "A" in FIG. 4B.

FIG. 4B is a schematic showing a longitudinal cross-section of the drive tube.

FIG. 4C is a schematic showing a transverse cross-section of the drive tube along plane "C" in FIG. 4B.

FIGS. 10A and 10B are schematics showing multiple configurations of the torque limiter assembly.

DETAILED DESCRIPTION

Figure 1:
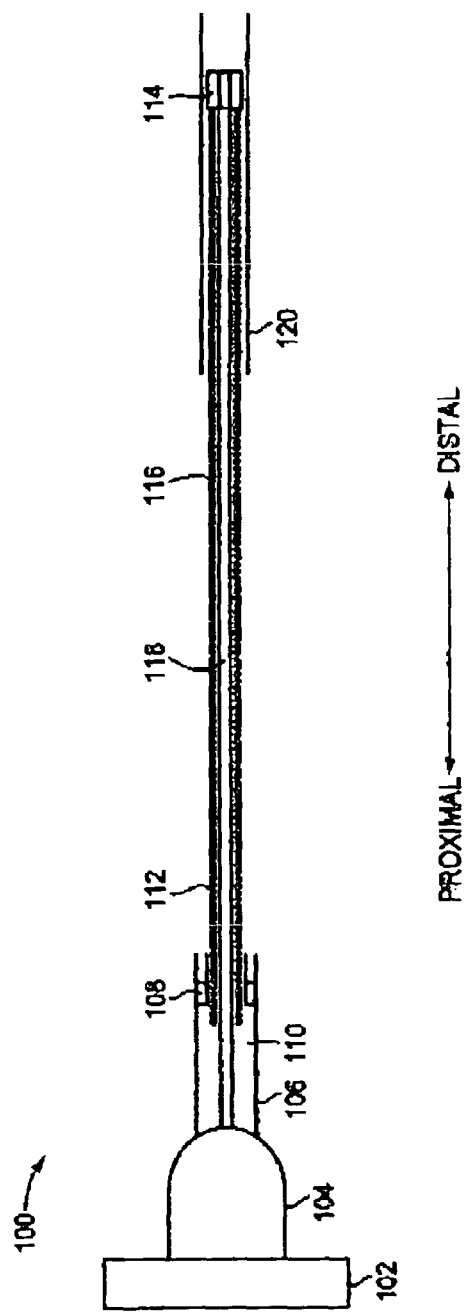
FIG. 1 shows a schematic of an imaging core assembly.

An intralumenal imaging system generally comprises an imaging core that is mechanically coupled to a motor 102 that spins one or more components of the imaging core. FIG. 1 shows a schematic diagram of a rotating imaging core 100, in accordance with an illustrative embodiment. Rotatable imaging core 100 can include one or more of, from proximal to distal, a connector 104 such as an optical connector and/or an electrical connector, which in turn drives a drive tube 106 and/or an optical fiber or wire 118. An optical fiber is used to transfer optical signals such as signals from an optical coherence tomography probe. A wire can be used in the imaging core 100 to transfer IVUS signals or other electrical signals. A spacer tube 108 is secured in the lumen 110 of the drive tube by interference fit and acts as a frictional torque limiter. Spacer tube 108 is attached to the torque wire 112, for example, at or near the proximal end of the torque wire. A second end of torque wire 112 is attached to an imaging probe 114 (e.g., OCT, IVUS, or combination OCT/IVUS or OCT/FFR probe). During use, optical connector 104, drive tube 106, spacer tube 108, torque wire 112, and imaging probe 114 spin in unison because the interference fit creates sufficient friction between the spacer tube 108 and the drive tube 106 to withstand normal torsional forces. However, if torque wire 112 or imaging probe 114 binds to the catheter during use, spacer tube 108 slips within the drive tube. Spacer tube 108 acts as a clutch that allows torque wire 112 to stop or spin at a slower rate than drive tube 106 until the motor 102 is stopped.

With continued reference to FIG. 1, torque wire 112 forms a lumen 116 that carries an optical fiber or wire 118. The optical fiber or wire connects the connector 104 to the imaging probe 114. In some embodiments, torque wire 112 extends from the imaging probe 114 to spacer tube 108, but torque wire can extend partially or entirely through the spacer tube and as far as optical 104 if desired. A delivery sheath or catheter 120 is used to insert the torque wire 116 and imaging probe 114 into a body lumen, such as a blood vessel. In preferred embodiments, the drive tube and spacer remain outside the patient's body. The delivery sheath 120 does not rotate. In some embodiments, the torque wire 112 does not extend completely to the lens 114. In some embodiments, other torsional devices are used instead of a torque wire, such as a thick coating on the fiber.

FIG. 2A shows a longitudinal cross-section of a torque limiter assembly 200 comprising drive tube 106, spacer tube 108, and torque wire 112, in accordance with an illustrative embodiment. Drive tube 106 is connected by its proximal end directly or indirectly to the connector (104 in FIG. 1). Drive tube 106 can be made of any suitable material such as metal and, for example, a shape memory metal such as Nitinol. Spacer tube 108 is disposed in the distal end of drive tube 106. Spacer tube 108 fits within the drive tube lumen 110 by an interference fit that causes friction between the outside diameter of the spacer tube and inside diameter of the drive tube. For example, the outside diameter of the spacer tube 108 can be slightly larger than the diameter of the drive tube lumen 110.

In some embodiments, spacer tube 108 forms a protrusion 204 and the protrusion is configured to cause an interference fit with the drive tube wall. Protrusion 204 can be any suitable shape that provides sufficient friction between the spacer tube 108 and the drive tube 106. In some embodiments, protrusion 204 is a circumferential collar that has a width 205. In some embodiments, the spacer tube 108 has a substantially uniform diameter (see FIG. 12). In some embodiments, the spacer tube 108 has a chamfered collar (see FIG. 19). In some embodiments, the spacer tube 108 forms a plurality of ribs that cause the interference fit (see FIG. 21).

Torque wire 112 is securely attached to spacer tube 108, such as by glue or welding 208 so that rotational force applied to the spacer tube is transferred to the torque wire. The torque wire is attached at least to the distal end of the spacer tube, and can be partially or completely inserted through the lumen 111 of the spacer tube.

The spacer tube 108 and the drive tube 110 mate by interference fit. They are not attached (e.g., welded or glued). This interference fit transmits torque from the patient interface unit (PIU) motor 102, through connector 104, into drive tube 106, through the interference fit to spacer tube 108 and finally to torque wire 112 and imaging probe 114. Should torque wire 112 experience unsafe binding to the non-rotating sheath or catheter 120 which covers it, spacer tube 108 will slide within drive tube 106 at the interference fit. The torque transmitted will decrease as sliding friction is lower than static friction and additional torque and rotations of the sheath cannot be generated. As spacer tube 108 spins inside the drive tube 106, the optical fiber or wire 118 winds up. After a few winds the optic fiber or wire 118 breaks, and loss of signal can automatically trigger the motor 102 to stop, ending the unsafe condition. In some embodiments, fiber or wire breakage is detected using software. The frictional torque limiter therefore provides an immediate response to unsafe torque levels until the motor can be stopped.

Referring to FIG. 2B, a perspective view of a torque limiter assembly 200 is shown, in accordance with an illustrative embodiment. The interference fit between the spacer tube 108 and the drive tube 106 is created using a slit 206 in the drive tube 106. Slit 206 is cut parallel to the centerline of drive tube 106. Slit 206 can be any suitable length, for example between about 0.25 and about 1.5 inches and, more preferably, about 0.75 inches in length. Slit 206 extends to one end of the drive tube 106.

FIG. 3A shows a longitudinal cross-section of a torque limiter assembly having an inverted spacer tube. The components of this assembly are similar to FIG. 2A, however, spacer tube 108 has been inverted such that protrusion 204 is on the proximal end of the spacer tube, rather than on the distal end of the spacer tube as shown in FIG. 2A. In this embodiment, the distal end of spacer tube 106 can extend beyond the distal end of drive tube 106, but the spacer also can be fully disposed in the drive tube. In some embodiments, protrusion 204 is a circumferential collar that has a width 305.

FIG. 3B shows a perspective view of a torque limiter assembly having an inverted spacer tube. The components of this assembly are similar to FIG. 2B, however, spacer tube 108 has been inverted such that protrusion 204 is on the proximal end of the spacer tube. Again, the distal end of spacer tube 106 can extend beyond the distal end of drive tube 106, but the spacer also can be fully disposed in the drive tube.

Referring to FIGS. 4A-4C, a more detailed schematic of the drive tube is shown, in accordance with an illustrative embodiment. FIG. 4A is a schematic showing a transverse cross-section of the drive tube along plane "A" in FIG. 4B. In preferred embodiments, the drive tube 106 is made of Nitinol and the drive tube has an outside diameter 302 of about 0.0390±0.0008 inches and an inside diameter 304 of about 0.0330±0.0005 inches, although other dimensions can be used. In preferred embodiments, the Nitinol has a minimum ultimate tensile strength of 155 KSI, a plateau of 55 KSI, a permanent set of 0.3%, and elongation failure of >10%. The drive tube can be manufactured by drawing.

FIG. 4B is a schematic showing a longitudinal cross-section of the drive tube. The drive tube is substantially cylindrical in shape. In preferred embodiments, drive tube 106 is 9.600±0.025 inches in length, but can be any suitable length. A slit 206 is cut parallel to the centerline of the drive tube. Slit extends from one end of the tube 107 partially along the length of the tube. Slit 206 has a closed end 207. Element 306 corresponds to the overall drive tube length, which in a preferred embodiment is 9.6 inches. Element 308 corresponds to the length of the slit. In one embodiment, the slit has a length of 0.75 inches and a substantially uniform width 310 of about 0.0015 inches. However, longer and wider slits can be used. A laser cutting or electrolytic process can be used to cut the drive tube to length, to cut the slit, and to break the edges on both ends of the tube. An abrasive solution can be run through the lumen of the tube after cutting.

FIG. 4C is a schematic showing a transverse cross-section of the drive tube along plane "C" in FIG. 4B. In preferred embodiments, one slit 206 is formed in the drive tube 206. Preferably, any burrs from the manufacturing process are removed from the inside surface of drive tube 106 to ensure a reliable interference fit between the drive tube and spacer tube.

The spacer tube also is substantially cylindrical in shape. In preferred embodiments, spacer tube 108 has an outside diameter of 0.035 inches and an inside diameter of 0.023 inches, and is manufactured by Swiss machining. Thus, the outside diameter of the spacer tube is slightly larger than the inside diameter of the drive tube. The spacer tube is made of 300 series stainless steel, in one embodiment. In another embodiment, the spacer tube is made of aluminum.

The interference between the spacer tube and the drive tube has a tight tolerance. Preferred dimensions and tolerances are provided in Table 1.

TABLE 1

Fabrication Tolerances.

| Component | Size (inches) | Dimension | Fabrication Technique | Tolerance (inches) |
| --- | --- | --- | --- | --- |
| Drive tube | 0.039 OD, 0.033 ID | ID | Drawing | +/−0.0005 |
| Spacer tube | 0.035 OD, 0.023 ID | OD | Swiss machining | +/−0.0002 |

Using the sum of tolerances, a conservative method, the interference fit between the drive tube and space tube can vary by ±0.0007 inches. This tight tolerance is sufficient to provide a repeatable torque at which the joint consistently slips. The following analysis can be used to calculate the torque value:

The coefficient of static friction controls the limiting torque value. The static friction ($\mu$) for steel on steel is:

$\mu=0.8$

The frictional force (F) is:

$F=\mu N$

Where $N$=the normal force between the drive tube and the spacer tube

The limiting torque (T) is:

$T=rF$

Where $r$=the radius of the protrusion on the spacer (half the diameter).

When the spacer tube is inserted into the drive tube, the slit in the drive tube opens up from the interference fit. Once the spacer tube is inserted and the slit expanded, the drive tube no longer is round as a result the interference fit. Thus, the interference force is not uniform around the spacer. FIG.

5 shows the interference forces calculated by a finite element simulation of the spacer tube and drive tube, based on the dimensions provided in Table 1.

Figure 5:
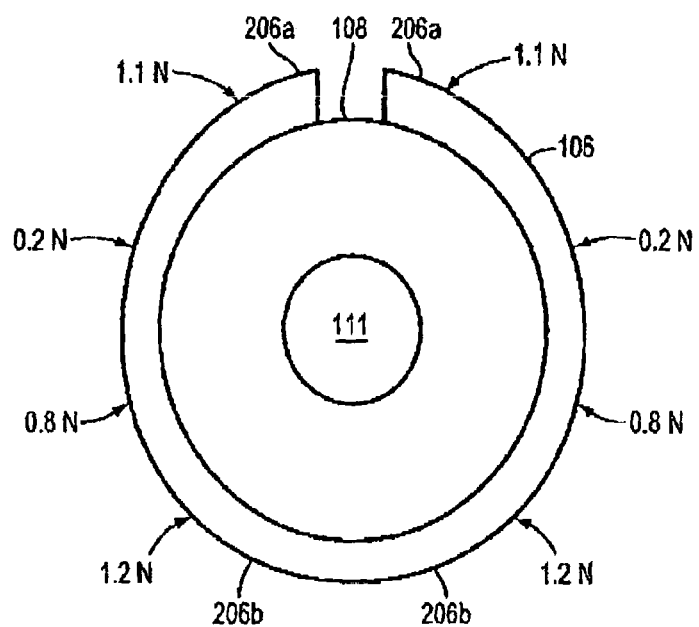
FIG. 5 shows a transverse cross-section of a torque limiter assembly showing interference forces between the spacer tube and the drive tube.

FIG. 5 shows a transverse cross-section of a torque limiter assembly showing interference forces between the spacer tube 108 and the drive tube 106. The highest forces are at the edges of the slit 206a and on the walls opposite the slit 206b. This concentration of forces is expected because of the radius of curvature of the slitted drive tube is smaller than that of the spacer tube. There are also non-normal forces to the interference but these may not materially contribute to the friction of the parts. After summing the forces shown in FIG. 5, the maximum torque value can be calculated using the above analysis.

Figure 6A:
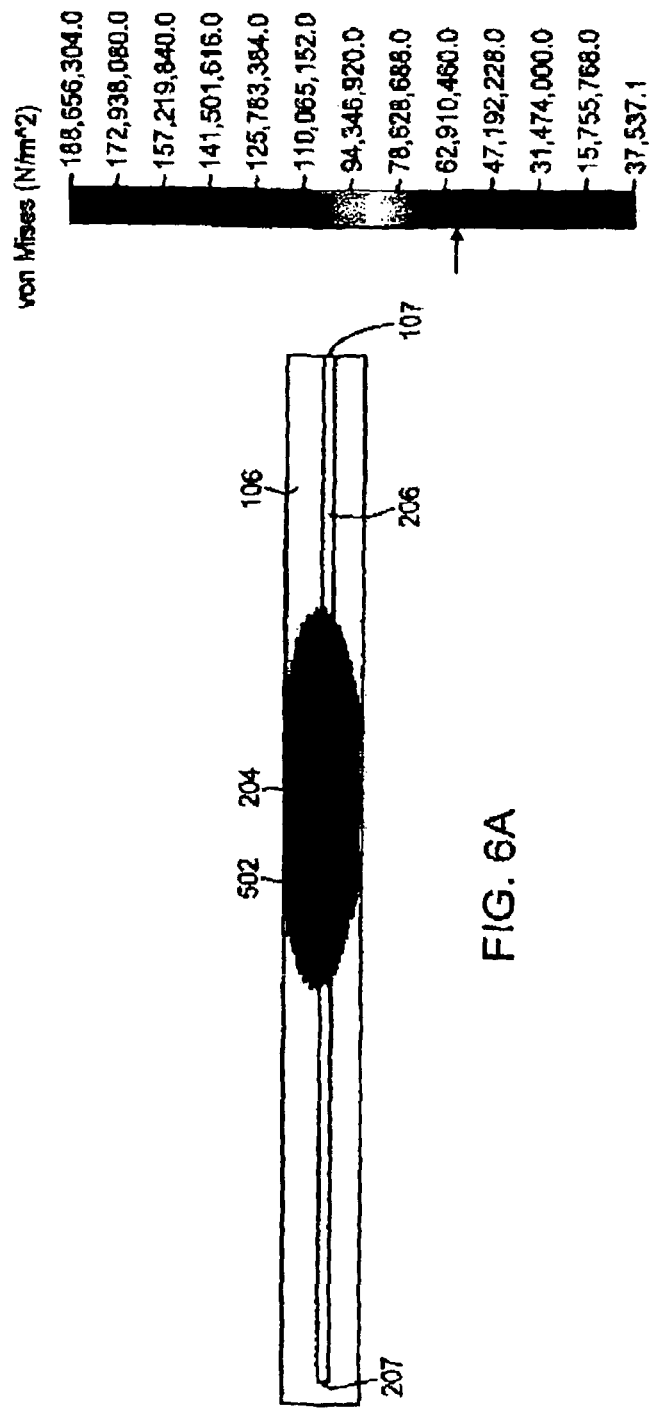
FIG. 6A shows a stress map of the interference fit between the spacer tube and the drive tube when the spacer tube protrusion is approximately centered along the slit.
Figure 6B:
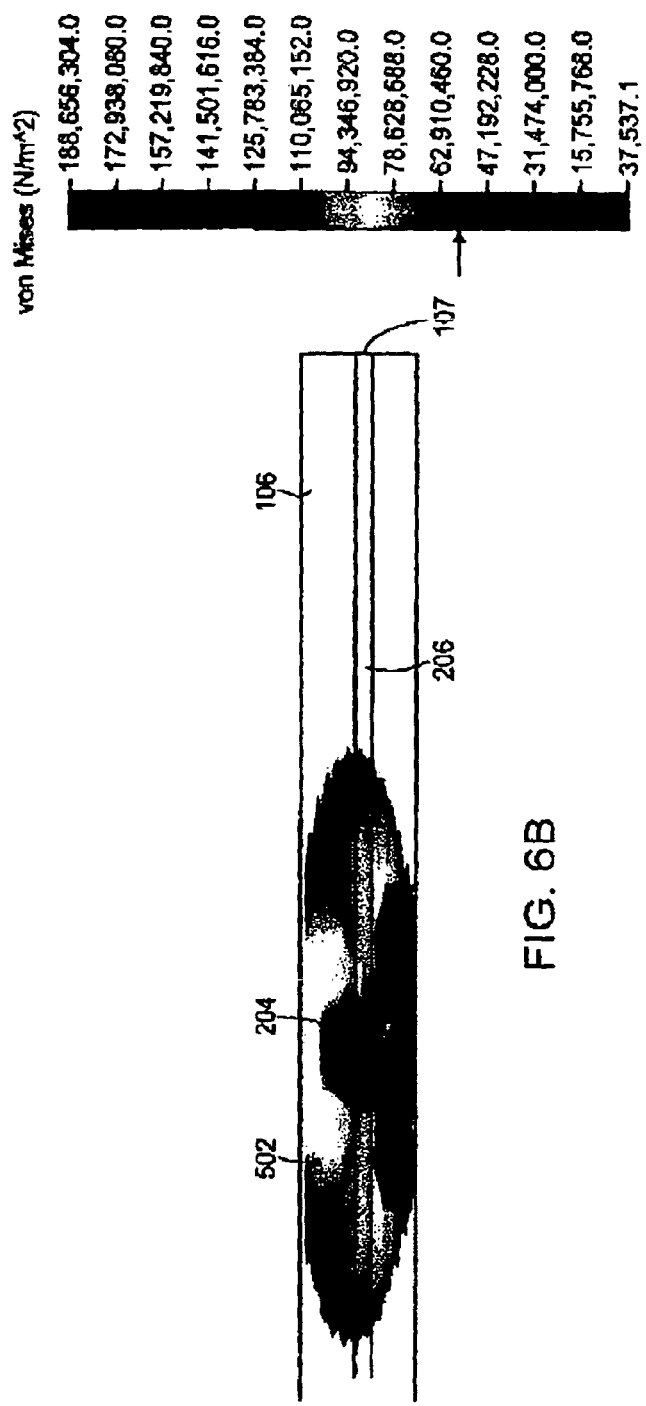
FIG. 6B is a zoomed in view of FIG. 6A.

FIG. 6A is a stress map showing the interference fit between the spacer tube and the drive tube, when the spacer tube is approximately centered along the slit. The area of high stress 502 is shaded. The area of stress 502 is confined to just around the protrusion 204 of the spacer tube 108. The stress is what causes the normal force—i.e., the interference—between the drive tube and the spacer tube. The drive tube end 107 and slit end 207 do not contribute to the stress in this configuration. Spacer tube 108 does not significantly deform and thus its internal geometry is not critical to the normal force. FIG. 6B is a zoomed view of FIG. 6A. Stresses above 60 MPa are colored. The highest stress is 190 MPa, which is below the stress Nitinol would permanently deform. Permanent deformation is not desirable as it would reduce the normal force between the slitted tube and the spacer. Stress is greater and more extensive on the side opposite the slit. This indicates that the side opposite the slit is contributing more to the normal forces than the region around the slit.

Figure 7:
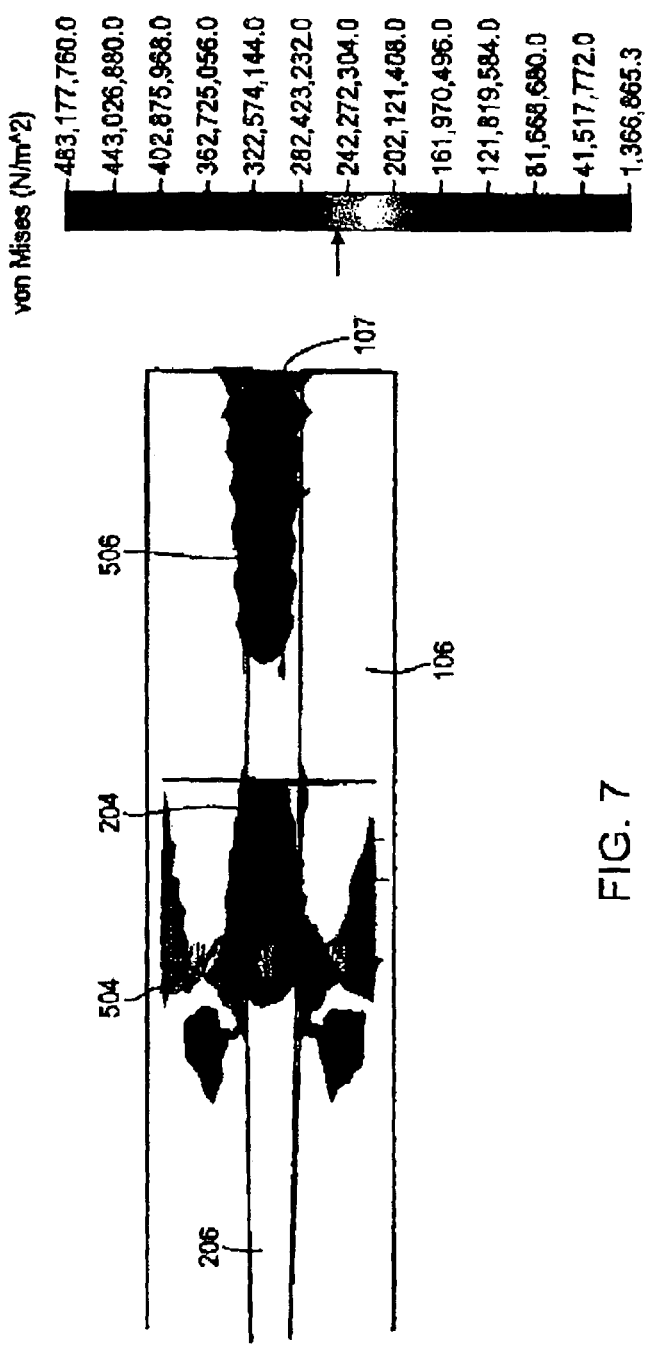
FIG. 7 shows a stress map of the interference fit when the spacer tube protrusion is positioned towards the open end of the drive tube slit.
Figure 8:
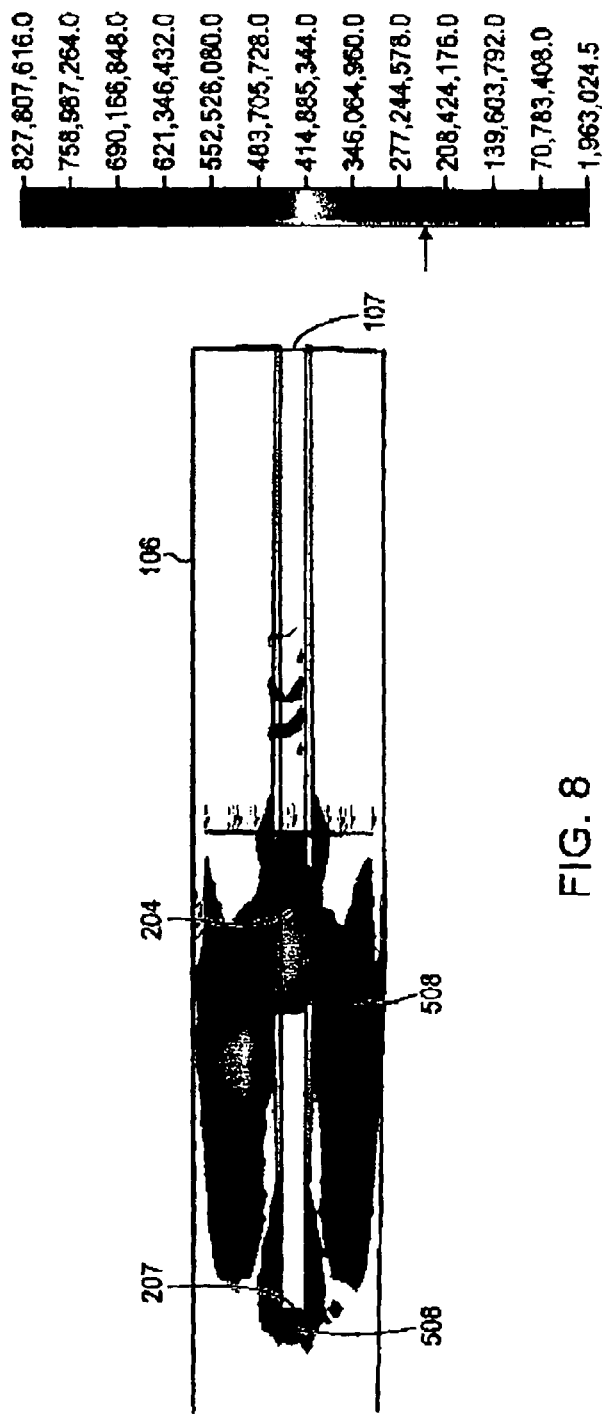
FIG. 8 shows a stress map of the interference fit when the spacer tube protrusion is positioned towards the closed end of the drive tube slit.

FIG. 7 shows a stress map of the interference fit when the spacer tube is positioned towards the open end of the drive tube slit. Areas of high stress 504 and 506 are shaded, and are localized to the areas around the protrusion 204 of the spacer tube 108 and the open end of the drive tube 107, respectively. The open end of the drive tube 107 shows significant deformation, which lowers the normal force at the interference fit—i.e., around the spacer tube projection 204—which results in a looser fit. The forces in FIGS. 7 and 8 are higher than those in FIG. 6B because a larger interference was chosen. The stress concentration location will not change at a lower interference.

FIG. 8 shows a stress map of the interference fit when the spacer tube is positioned towards the closed end of the drive tube slit. The area of high stress is shaded 508, and encompasses the area surrounding the closed end of the slit 207 and the protrusion 204 of the spacer tube 108. The closed end of the slit 207 exerts significant force, which increases the frictional force at the interference fit—i.e., around the spacer tube projection 204—which results in a tighter fit.

Figure 9A:
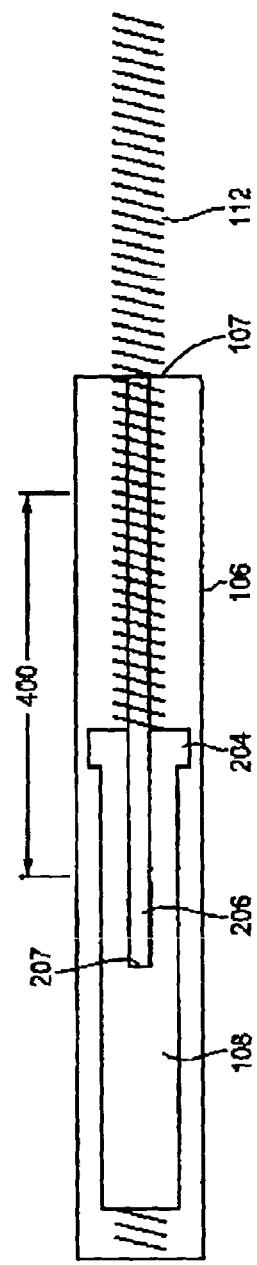
FIG. 9A is a schematic showing optimal positioning of the spacer tube with respect to the drive tube slit.

FIG. 9A is a schematic showing exemplary positioning of the spacer tube with respect to the drive tube slit. The geometry of the drive tube slit creates a region of minimally variant torque 400 away from the closed end of the slit 207 and away from the open end of the drive tube 107. In this central slit region 400, torque does not vary significantly with the insertion depth of the spacer. Thus, the precise alignment of the spacer tube projection 204 to the drive tube 106 is not critical, which facilitates assembly of the torque limiter and reduces the variability of the maximum torque. Consequently, the spacer tube 108 can be attached (e.g., welded) to the torque wire 112 and simply inserted into the drive tube 106 until the spacer tube projection is positioned within central slit region 400. In one embodiment, a portion of the spacer tube, such as a portion of a projection or a surface of the spacer tube wall, is disposed within the region of minimally variant torque. In one embodiment, the length of the region of minimally variant torque ranges from about 0.25 inches to about 1.25 inches.

Figure 9B:
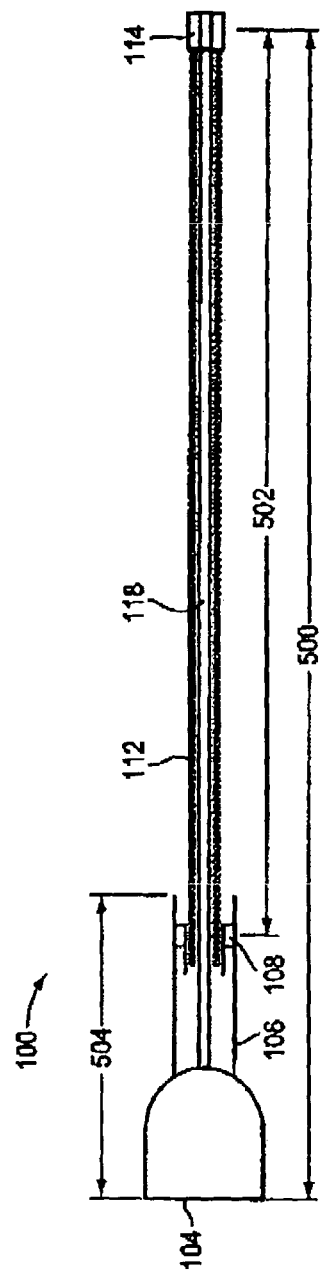
FIG. 9B is a schematic showing tolerances for optimal positioning of the spacer tube with respect to the drive tube slit.

The length of the slit is chosen such that over the tolerance of the optical core, the spacer will be located in an area where the breakaway torque will be invariant of position. The tolerances of the spacer welding to the torque wire and the optical length determine the location of the spacer in the slit. Referring to FIG. 9B, which shows a rotating image core in accordance with an illustrative embodiment, the relationship and tolerances of the components are as follows:

Optical Length Tolerance (OL)=length of the optical fiber from the connector to the imaging probe+/−5 mm (500 in FIG. 9B);

Spacer tube+torque wire length Tolerance (TW)=Length from the spacer tube protrusion to the torque wire end+/−2 mm (502 in FIG. 9B);

Drive tube+connector length tolerance (NI)=Length from the connector to the end of the drive tube+/−1 mm (504 in FIG. 9B);

Accordingly, the spacer tube location tolerance (SP) is defined by:

$$SP=OL+TW+NI=+/-5+/-2+/-1=+/-8 \text{ mm}=+/-0.31 \text{ inches.}$$

This is well within the invariant torque length of +/−0.5 inches

Frictional torques can be calculated over the expected range of interferences. Table 2 shows frictional torques calculated based on the expected range of interferences. Based on the formulas above, the following is the frictional torque variation over the tolerance range of the drive tube and the spacer tube:

TABLE 2

Friction torques.

| Interference | Torque (oz-in) |
| --- | --- |
| 0.005 | 0.10 |
| 0.012 (Nominal) | 0.24 |
| 0.019 | 0.40 |

Thus, the upper limit is about 4.0 times the lower limit. This range would be decreased if the nominal interference was increased. The spinning of the spacer tube in the drive tube is not destructive. Thus, each drive tube and spacer tube can be tested after manufacture for quality control, if desired.

To increase the nominal interference for the same torque, a number of options can be pursued such as, for example, coating the outside diameter of the spacer tube from a material that has a lower coefficient of friction such as Teflon or reducing the wall thickness of the drive tube from about 0.003 inches to about 0.002 inches.

FIGS. 10A and 10B show two configurations of the torque limiter assembly 200, in accordance with illustrative embodiments. Referring to FIG. 10A, the spacer tube protrusion 204 is located on the proximal end of the spacer tube 108. In this configuration, the spacer tube 108 can extend outside the drive tube 106, thereby making the torque wire attachment point 208 (e.g., a weld) visible during final inspection. It would also permits attachment of the torque wire 112 after the spacer tube 108 is inserted into the drive tube 108 to a preselected location. If the spacer tube 108 extends outside of the drive tube 106, it creates a lever arm 402 that would increase the variability of the maximum torque when the joint is bent. The section of the spacer inside the tube 404 resists the lever arm.

Referring to FIG. 10B, if the spacer tube protrusion 204 is on the distal end of the spacer tube 108, the spacer tube 108 is always inside the drive tube 106 and the lever arm effect is eliminated. In this configuration, the spacer tube 108 is attached to the torque wire 112 before the spacer tube 108 is inserted into the drive tube 106.

The spacer tube protrusion also can be located in the in central portion of the spacer tube. Multiple protrusions also can be used and would help anchor the spacer tube in the drive tube with the disadvantage that a longer slit length would be needed to keep the spacer tube in the region of invariant torque. Alternatively, a longer single protrusion would behave similarly to multiple protrusions. The torque wire can go through all or a portion of the spacer tube, or the torque wire can be butted against the spacer tube. The spacer tube and torque wire can be attached anywhere along the length or ends of the spacer tube.

Figure 11:
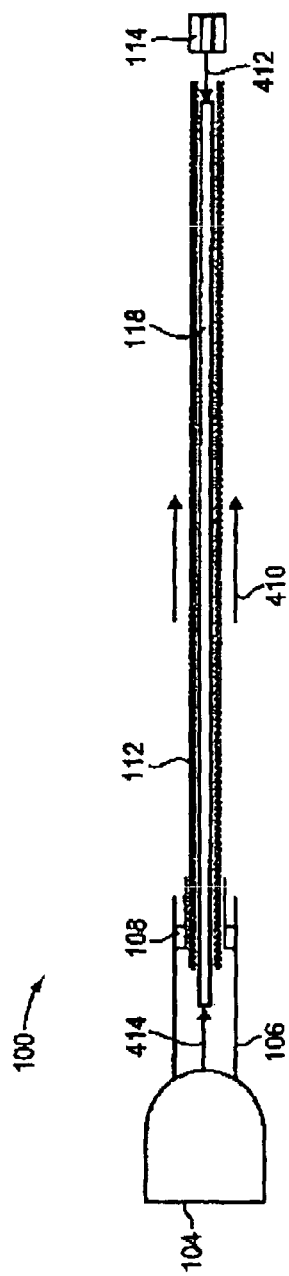
FIG. 11 shows a schematic of the tensile forces on an imaging core.

During use, a portion of the imaging core is inserted to a target location within a body lumen. The imaging core then is rapidly pulled back relative to the catheter or sheath, which remains relatively stationary. Faster pullback speeds allow for shorter flush times, which reduce flush agent use and the amount of time the vessel is without blood. As pullback speeds increase, however, the tensile forces on the image core also increase. The present invention is suitable for use with high pullback speeds. FIG. 11 shows a schematic of the tensile forces on an imaging core. As the image core is quickly pulled back during image acquisition, from friction with the sheath, the torque wire 112 is pushed 410 distally. The torque wire can be attached to the optic fiber or wire 118 at the imaging probe 114. The imaging probe 114 pulls on the optic fiber or wire 118, which is stretched 412. Since the optic fiber or wire 118 is much stiffer in tension than the torque wire 112, the optic fiber or wire 118 takes up this tensile load. The optic fiber or wire 118 transfers this load 414 to the connector 104 which then transfers the load to the pullback mechanism in the motor.

In tight bends, such as in a blood vessel, the friction between the imaging core sheath and the torque wire can approach 0.1 pounds. Assuming a 125 μm optic fiber is used, the optic fiber can easily withstand the 0.1 pounds load without breaking, however it will stretch by the following amount:

$$dL = \text{Change in length} = \frac{F * L}{E * A} = 0.032 \text{ in}$$

Where:
F=Friction force on fiber=1 lb
D=Fiber OD: 125 μm
L=Fiber length: 164 cm
E=Fiber Modulus: 73 GPa
A=the fiber area (pi D^2/4)

Thus, a 0.1 pound force stretches the whole optic fiber by 0.032 inches. This stretch is taken up by the torque limiter assembly. Thus it can elongate by as much as 0.032 inches (0.8 mm). The spacer tube can move by this amount relative to the drive tube, but with the preferred embodiment the spacer tube protrusion remains in the location of invariant torque (400 in FIG. 9A) and the torque limiter assembly will operate within specifications. Since the optic fiber is not attached to the torque wire, the optic fiber's stretching will have no significant localized effects on the short length of the drive tube slit (206 in FIG. 9) and also will have no significant effect on the torque limiter assembly.

In addition, 0.032 inches of stretch is not seen in practice because the torque wire is very stretchy compared to the fiber. Consequently, the torque wire takes up most of the stretch, not the torque limiter assembly.

A variety of spacer tube configurations can be used in accordance with the invention. For example, FIGS. 10A and 10B show preferred embodiments. Spacer tube 108 in FIG. 10A has a circumferential collar protrusion 204 on a proximal end of the spacer tube. Spacer tube 108 in FIG. 10B has a circumferential collar protrusion 204 on the distal end of the spacer tube. The short width of these protrusions keeps the region of invariant torque as long as possible, whereas the increased overall length of the spacer minimizes sensitivity to bending. The preferred radial step size between the spacer and the protrusion is about 0.0015 inches.

Figure 12:
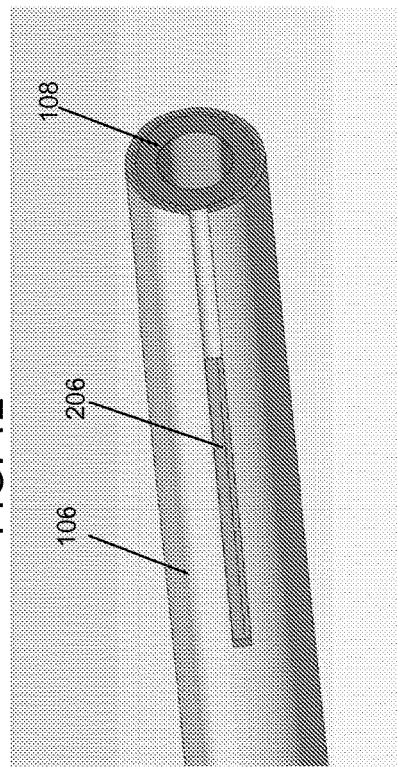
FIG. 12 shows a perspective view of a spacer tube having a substantially uniform diameter.
Figure 13:
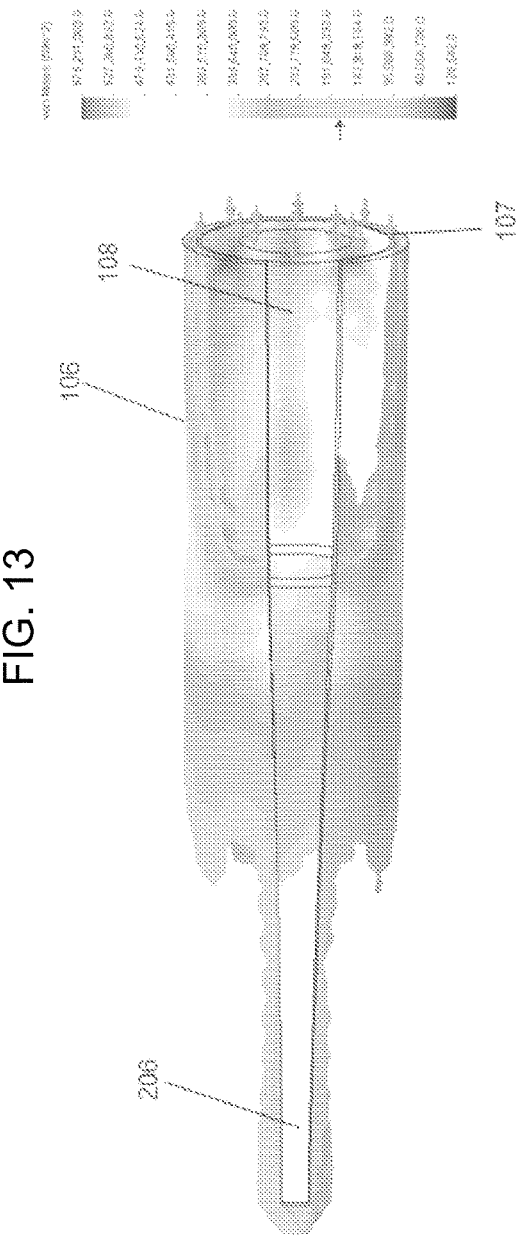
FIG. 13 shows a stress map of the interference fit when the spacer tube has a substantially uniform diameter and is placed at the open end of the drive tube slit.

FIG. 12 shows a perspective view of a spacer tube 108 having a substantially uniform diameter along its length. FIG. 13 shows a stress map of the interference fit when the spacer tube has a substantially uniform diameter and is placed at the open end of the drive tube slit. Due to the substantially uniform diameter of the spacer tube, the end of the drive tube deforms significantly. FIG. 13 is based on a finite element simulation. The friction force on the spacer tube changes depending upon the depth of insertion into the drive tube 106. The further the spacer tube is inserted, the greater the friction force. Thus, this design is sensitive to the location of the spacer tube 108 on the drive tube 106.

When the drive tube is made of Nitinol, the strain on the drive tube when the spacer tube is inserted is about 0.5%. Nitinol can take strains of up to about 5% before undesirable permanent deformation occurs. Thus, Nitinol has a significant margin above the maximum strain of the mating parts. On the other hand, stainless steel will show a permanent deformation at 1% strain, which means it is practical but not with much margin, especially if the break away region is subjected to bending during operation. While Nitinol is preferred, the drive tube can be made of any suitable shape metal.

Figure 14:
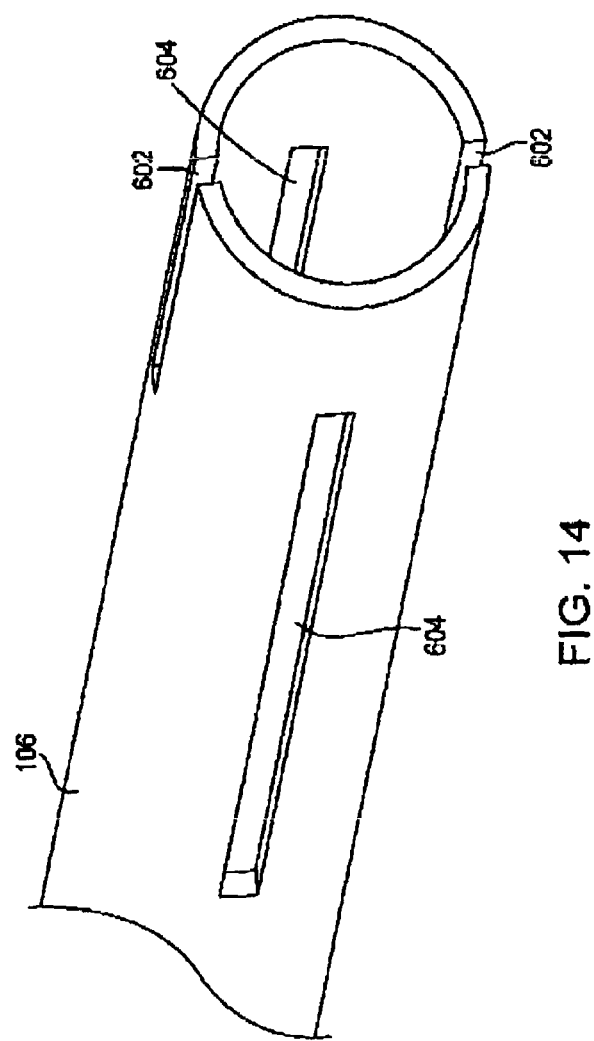
FIG. 14 shows a perspective view of a drive tube having multiple slits and slots.

FIG. 14 shows a perspective view of a drive tube having multiple slits and slots. Drive tube 106 has two opposing slits 602 (i.e., cuts having one open end and one closed end) and two opposing slots 604 (i.e., cuts having two closed ends). The slits are oriented transversely to the slots. As a result, of the extra cuts, drive tube 106 becomes so flexible that slots 604 cannot extend to the end of the tube, otherwise the end would split. If the drive tube slit is eliminated altogether, the drive tube and spacer tube could be press fit with the spacer tube inside the drive tube.

The friction force created by a single slit is provided by the compression of the circular shape of the drive tube. This is repeatable, as the wall thickness and inside diameter are well controlled. If additional cuts are added to the drive tube, then the end of the cuts become important in maintaining the interference fit. In addition, the lower strength of the tube would make the design more sensitive to bending. A single slit in the drive tube avoids these drawbacks and also is easier to manufacture, and therefore is preferred.

Figure 15:
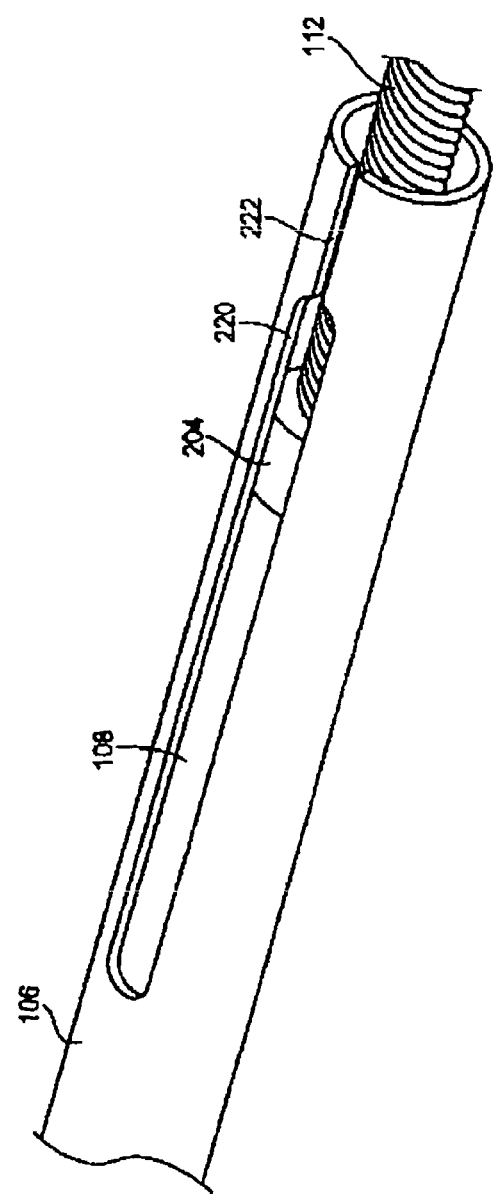
FIG. 15 shows a perspective view of a drive tube having a widened slit.

In some embodiments, a wider slit is used. FIG. 15 shows a perspective view of a drive tube having a widened slit. As shown in FIG. 15, a laser is used to cut a wide slit 220. This lowers the total normal force. A wider slit 220 can be used to reduce the average maximum torque for the same interference fit. The slit gets narrower 222 towards the end of the drive tube 106. This improves the retaining of the torque wire 112 and it presents a smoother surface at the end of the drive tube 108. This also prevents the drive tube 106 from cutting the imaging core sheath.

Figure 16:
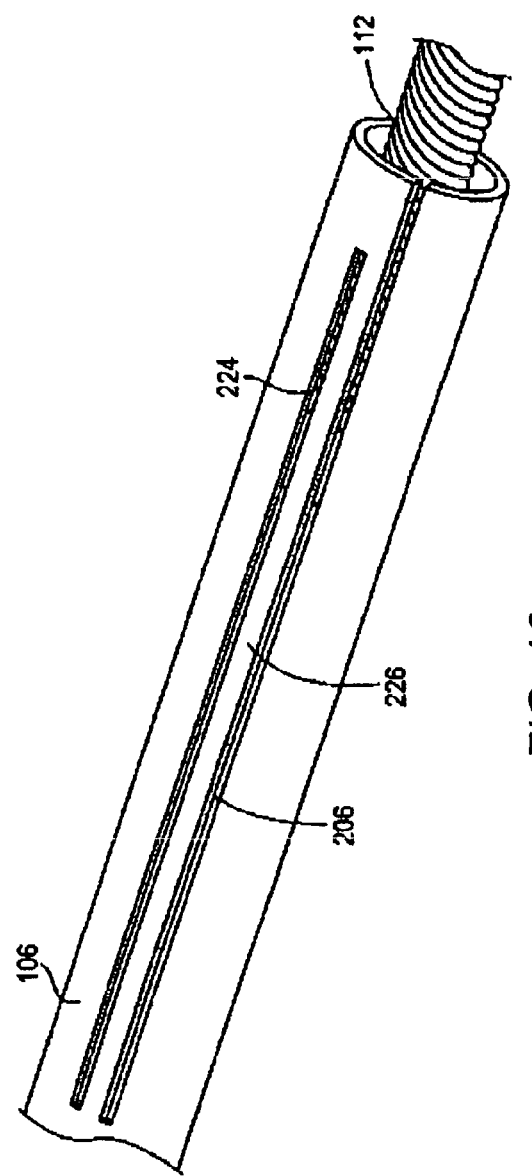
FIG. 16 shows a perspective view of a drive tube having a slot and a slit.

FIG. 16 shows a perspective view of a drive tube having both a slot and a slit. A slot 224 is cut parallel to slit 206 and the material between the slot and the slit 226 is left intact. Placing the slot and the slit too close compromises drive tube integrity and reduces normal forces, so this is to be avoided.

Figure 17:
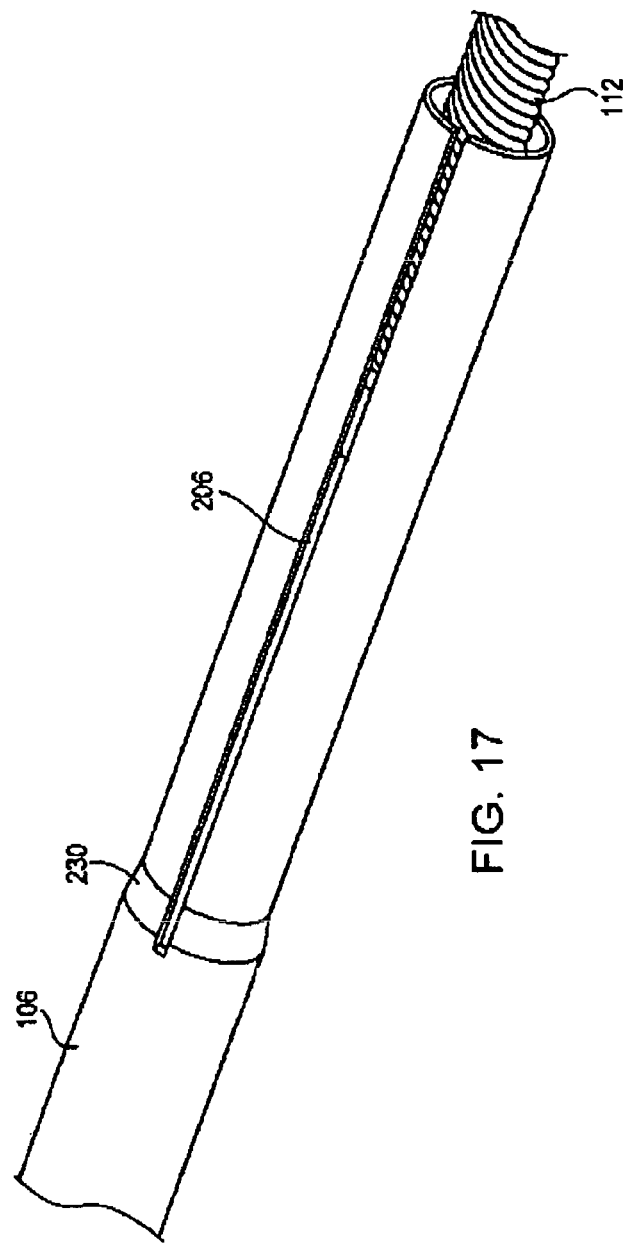
FIG. 17 shows a perspective view of a drive tube having a reduced wall thickness along the slit.

FIG. 17 shows a perspective view of a drive tube having a reduced wall thickness along the slit. As an alternative to making the slot wider, torque can be reduced by reducing drive tube wall thickness 230 along the slit 206. The wall thickness 230 may be varied based on the measurements of the inside diameter to obtain a more uniform maximum torque. The inside diameter is measured on a lot of tubes. If the inside diameter is small, more material is ground off the outside diameter.

Currently at a nominal torque value of 0.24 oz-in (from Table 2) the tensile strength of the design is the torque value divided by the radius of the spacer (0.0175 inches), which gives 0.85 lbs. As discussed previously, the fiber takes up the majority of the tensile load of the image core but additional strength can be gained from this torque limiter. 0.85 lbs is sufficient for this application. Having a repeatable tensile strength of this joint is desirable because, under some conditions, the image core could get caught during image core withdrawal and having a maximum tensile force of this joint helps the safety of the design.

Figure 18:
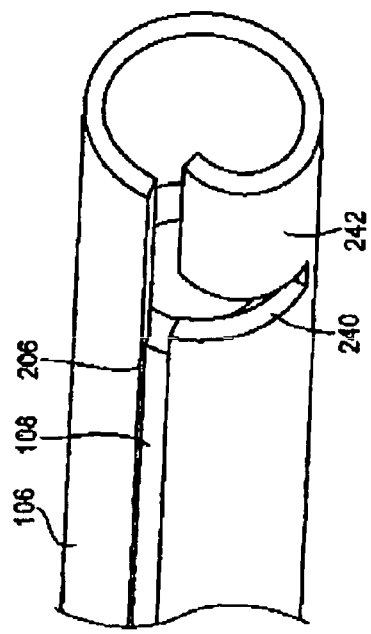
FIG. 18 shows a perspective view of a drive tube having a constrained end to prevent the spacer tube from escaping.

FIG. 18 shows a perspective view of a drive tube having a constrained end to prevent the spacer tube from escaping. The drive tube 106 has a slit 206 along the centerline of the drive tube. A second slit 240 near the end of the drive tube extends perpendicularly from slit 206. The second slit allows a portion of the drive tube wall to be folded inward as a tab 242. The tab 242 prevents the spacer tube 108 from coming escaping the drive tube 106 and it also takes some of the tensile load from the optic fiber during pullback. The bent tab 242 is made through a forming operation and requires heat treatment of the bent area to prevent fractures. This allows the joint to be much stronger in tension.

Figure 19:
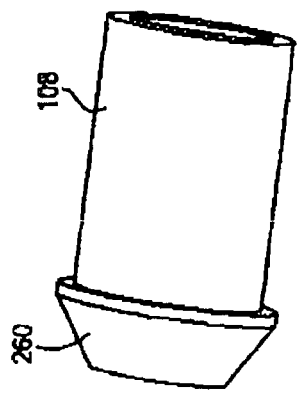
FIG. 19 shows a perspective view of a spacer tube having a chamfered collar.

FIG. 19 shows a perspective view of a spacer tube having a chamfered collar. The spacer tube 108 has a chamfered protrusion 260 that facilitates insertion into a driver tube during assembly. The chamfered protrusion 260 also creates the interference fit with the drive tube.

Figure 20:
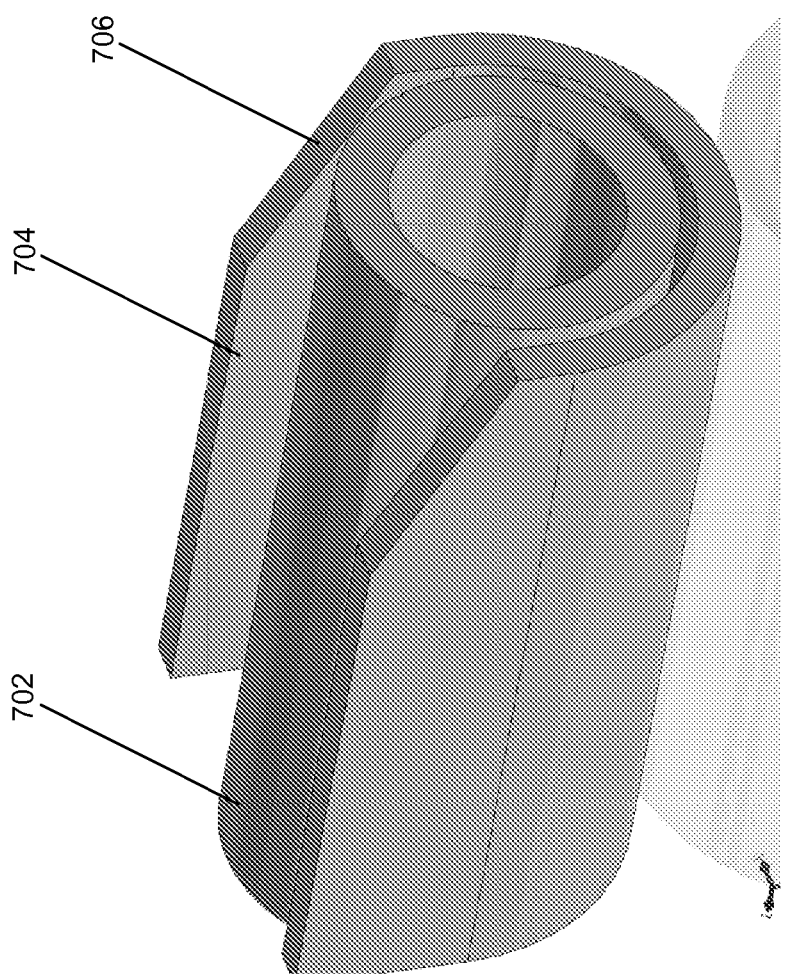
FIG. 20 shows a perspective view of flexible spacer tube.

FIG. 20 shows a perspective view of flexible spacer tube. The spacer tube 706 could be designed to flex and the drive tube 704 left unslitted. This embodiment shown has a piece of Nitinol wrapped around a stainless tube. The chamfers 706 at the ends allow for its insertion into the uncut Nitinol tube. The ends of the wrapped Nitinol tube would flex and press against the inside diameter of the Nitinol tube. This configuration is suitable for larger diameter tubes, but as size increases relative to the size of the distal image core the tighter the interference requirements become. For instance, if the diameter of the sliding surface is doubled, the friction force for the same torsional strength is halved. This is undesirable as the smaller the friction force, the tighter the tolerances on parts need to be for the same force variation. The two pieces may be fused together by a tack weld to ease assembly or they may be left separate.

Figure 21:
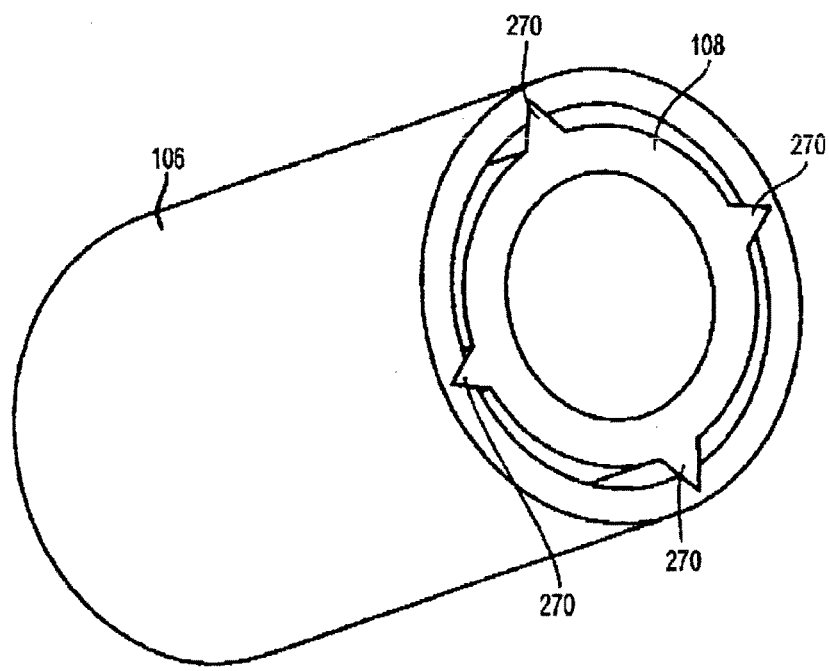
FIG. 21 shows perspective view of a spacer tube having rib projections.

FIG. 21 shows perspective view of a spacer tube having rib projections. A plurality of ribs 270 extend axially along the outer surface of spacer tube 108. The ribs are substantially straight and parallel, but can be arranged in other configurations. The ribs 270 are crushed as the spacer tube 108 is pressed into the drive tube 106. The drive tube in this embodiment is unslitted—i.e., it has no slits or slots. The spacer tube can be made of injection molded plastic.

An alternative would be to make the spacer tube out of Teflon or another material that would have a low bonding strength to glue and fill the joint between the drive tube (e.g., Nitinol) and the spacer tube with glue at an elevated temperature. Nitinol has a higher coefficient of expansion than Teflon and thus when the assembly cools the glue would have an interference fit to the Teflon. This could provide a repeatable break away friction.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

Throughout the application, where compositions are described as having, including, or comprising specific components, or where processes are described as having, including or comprising specific process steps, it is contemplated that compositions of the present teachings also consist essentially of, or consist of the recited components, and that the processes of the present teachings also consist essentially of or consist of, the recited process steps.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

What is claimed is:

1. A torque limiter for an intravascular imaging probe, the torque limiter comprising:
   a drive tube comprising a drive tube wall defining a drive tube lumen and an inside diameter, the drive tube wall defining a slit extending from a first end of the drive tube lumen along a portion of the drive tube wall;
   a spacer tube received in the first end of the drive tube lumen, the spacer tube comprising a spacer tube wall defining an outside diameter, at least a portion of the spacer tube wall being interference fit with the inside diameter of the drive tube wall such that there is a region of overlap between the spacer tube wall and the drive tube wall; and
   a torque wire attached to the spacer tube;
   whereby the spacer tube spins within the drive tube if torque on the torque wire exceeds a predetermined threshold.

2. The torque limiter of claim 1, wherein the spacer tube wall forms a circumferential collar and the circumferential collar is interference fit with the inside diameter of the drive tube wall.

3. The torque limiter of claim 2, wherein the circumferential collar is located at an end of the spacer tube.

4. The torque limiter of claim 3, wherein the circumferential collar has a chamfered edge to facilitate insertion into the drive tube.

5. The torque limiter of claim 3, wherein the circumferential collar is located in the spacer tube.

6. The torque limiter of claim 1, wherein the entire spacer tube wall is interference fit with the inside diameter of the drive tube wall.

7. The torque limiter of claim 1, wherein the slit extends axially along the drive tube wall.

8. The torque limiter of claim 1 comprising an optical coherence tomography probe coupled to an optical fiber disposed in the torque wire.

9. The torque limiter of claim 1 comprising an intravascular ultrasound probe attached to the torque wire.

10. The torque limiter of claim 1, wherein the interference fit has a torsional strength of 0.1 ounce-inches to 0.4 ounce-inches.

11. The torque limiter of claim 1, wherein the slit is wider at its closed end than at its open end.

12. The torque limiter of claim 1, wherein the drive tube wall has a thickness and the thickness is reduced along at least a portion of the slit.

13. The torque limiter of claim 1 comprising a slot parallel to the slit, the slot having closed ends.

14. A torque limiter for an intravascular imaging probe comprising:
a clutch comprising
a first rotatable tube defining a first bore, the first tube comprising a first tube wall defining a slit extending from a first end of the first rotatable tube, the first rotatable tube having a length T1; and
a second rotatable tube defining a second bore, the second tube comprising a second tube wall, the first rotatable tube having a length T2, the second rotatable tube disposed within the first rotatable tube such the first bore is concentric with the second bore, the second bore aligned to receive a torque wire below the slit, the second rotatable tube clutched by the first tube wall on either side of the slit such that the second rotatable tube is configured to slip or rotate if a torque on the torque wire exceeds a predetermined threshold.

15. The torque limiter of claim 14 further comprising the torque wire.

16. The torque limiter of claim 14 wherein T1 is greater than T2.

17. The torque limiter of claim 14 wherein the slit is wider at its closed end than at its open end.

18. The torque limiter of claim 14 wherein the second rotatable tube is interference fit within the first rotatable tube.

19. The torque limiter of claim 18 wherein the interference fit has a torsional strength of 0.1 ounce-inches to 0.4 ounce-inches.

20. The torque limiter of claim 19, wherein the second tube wall comprises a circumferential collar interference fit with an inside diameter of the first bore.

* * * * *